United States Patent [19]

Yoshida

[11] 4,249,319

[45] Feb. 10, 1981

[54] HEAT INSULATING INSERT FOR FOOTWEAR

[76] Inventor: Yoshiyasu Yoshida, 2-4-17 Kita Shinjuku, Shinjuku-Ku, Tokyo, Japan

[21] Appl. No.: 113,381

[22] Filed: Jan. 18, 1980

[51] Int. Cl.³ .................... A43B 7/02; A43B 3/10
[52] U.S. Cl. ............................. 36/2.6; 36/10
[58] Field of Search .................... 36/2.6, 10

[56] References Cited

U.S. PATENT DOCUMENTS

| | | | |
|---|---|---|---|
| 3,493,986 | 2/1970 | Erwin | 36/2.6 |
| 4,023,282 | 5/1977 | Ziegelheafer | 36/2.6 |
| 4,094,080 | 6/1978 | Sanders | 36/2.6 |
| 4,145,822 | 3/1979 | Mitchell et al. | 36/10 |

Primary Examiner—Patrick D. Lawson
Attorney, Agent, or Firm—Pearne, Gordon, Sessions, McCoy & Granger

[57] ABSTRACT

A heat insulating insert for a footwear which comprises a base sheet having a shape conforming with that of the sole of an average human foot and a toe cover at the toe portion of the base sheet for embracing the toe of the human foot. Porous bags containing exothermic agent therein are provided on the inner surface of the top of the toe cover and the toe portion of the base sheet in opposing and spaced relationship to the exothermic agent bag on the inner surface of the top of the toe cover and also in a portion of the base sheet corresponding to the plantar arch of the human foot. The exothermic agent performs exothermic reaction with the open air.

8 Claims, 2 Drawing Figures

U.S. Patent  Feb. 10, 1981  4,249,319
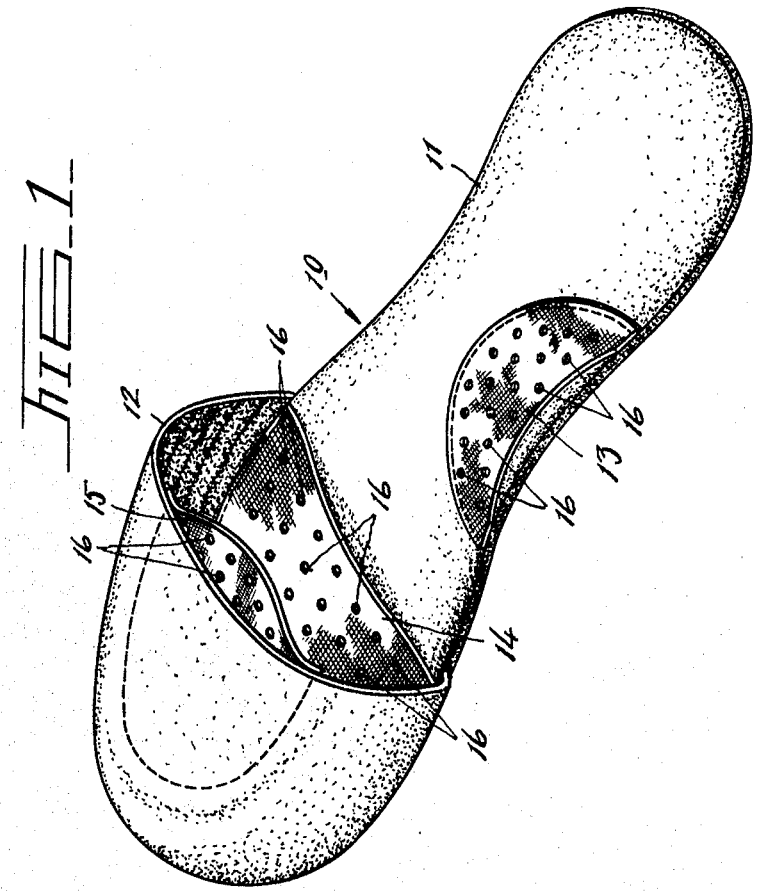
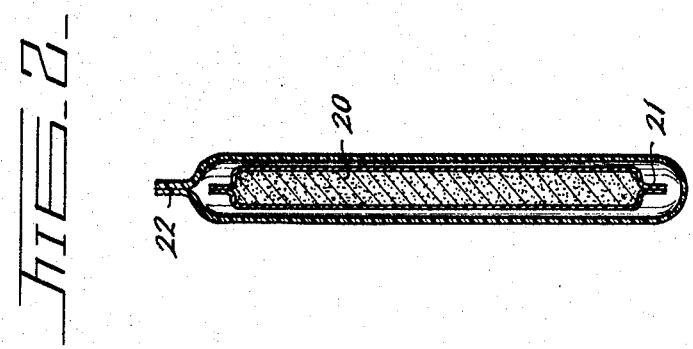

4,249,319

HEAT INSULATING INSERT FOR FOOTWEAR

BACKGROUND OF THE INVENTION

This invention relates to a heat insulating insert for footwears such as shoes, sandals and the like footwear.

There have been proposed and practically employed a variety of heat insulating footwears to keep the human feet placed in the footwears warm during cold weather seasons and one of the prior art heat insulating footwears employs a high heat insulating lining formed of fur, for example, to prevent the foot temperature from being lost to the open air. However, the prior art heat insulating footwear lining is not sufficient in heat insulating capability and the lining adds an undesirable thickness to the footwear to which the heat insulating lining is applied.

SUMMARY OF THE INVENTION

Thus, one object of the present invention is to provide means for effectively eliminating the disadvantages inherent in the prior art heat insulating footwears referred to hereinabove.

In order to attain the above purpose, the present invention provides a heat insulating insert for footwears which can positively heat the human foot placed in a footwear with a sufficient heat insulating capability to keep the foot warm during cold weather seasons.

The footwear heat insulating insert of the present invention can be easily placed in any conventional footwear without requiring any tool and processing work on the part of the footwear and includes exothermic agent at selected areas of the insert which contact parts of a human foot where the foot feels most chilly among various parts of the foot and especially, exothermic agent disposed at the area of the insert which corresponds to the plantar arch of the human foot performs massage on the plantar arch to accelerate circulation of blood in the foot in addition to its proper heat insulating function.

The above and other objects and attendant advantages of the present invention will be more readily apparent to those skilled in the art from a reading of the following detailed description in conjunction with the accompanying drawing which shows one preferred embodiment of the invention for illustration purpose only, but not for limiting the scope of the same in any way.

BRIEF DESCRIPTION OF THE DRAWINGS

FIG. 1 is a perspective view of one preferred embodiment of heat insulating insert for footwears constructed in accordance with the present invention; and FIG. 2 is a cross-sectional view on an enlarged scale of a porous storage bag which receives exothermic material therein for prior to the employment of the exothermic agent in the heat insulating insert of the invention.

PREFERRED EMBODIMENT OF THE INVENTION

The present invention will be now described referring to the accompanying drawing which shows one preferred embodiment of heat insulating insert for footwears according to the present invention.

The heat insulating insert of the invention generally comprises a main body 10 including a base sheet 11 which has a shape substantially corresponding to that of the sole of a human foot and a toe cover 12 at one end or the toe portion of the base sheet 11 corresponding to the toe of the human foot for receiving the toe of the human foot. Although the base sheet 11 and toe cover 12 may be optionally formed of a single sheet of leather, felt or synthetic rubber of a laminated sheet assembly of two or more layers of the materials, the base sheet is most preferably formed of a resilient material such as non-woven fabric because such material provides a cushioning function and although not shown, an anti-slip layer may be applied to a portion or the whole of the undersurface of the base sheet 11 as desired. Such an anti-slip layer can be formed by applying or printing rubber or vinyl chloride dissolved in a suitable solvent to or on a portion or the whole of the undersurface of the base sheet 11. In order to maintain the shape of a semi-circular cross-section as shown in FIG. 1 for accommodating the toe of a human foot, the toe cover 12 is preferably formed of a relatively hard material such as leather and if the toe cover is formed of felt, such felt is required to have a great fiber density. Furthermore, in order to perform exothermic reaction of exothermic agent 20 which is the heat insulating material employed in the insert and of which description will be made hereinafter, the base sheet 11 and toe cover 12 are required to have a degree of permeability and thus, if the base sheet 11 and toe cover 12 are formed of a relatively less permeable material such as leather or the like, the material is provided with a number of pores to make the base sheet 11 and toe cover 12 porous to thereby provide a required permeability for the parts of the insert.

The base sheet 11 has a semi-circular porous bag 13 disposed in a portion of the base sheet corresponding to the plantar arch of a human foot and also a second semi-circular porous bag 14 in a portion of the base sheet corresponding to the toe of the human foot. Similarly, a third semi-circular porous bag 15 is provided on the inner surface of the top of the toe cover 12 in an opposing and spaced relationship to the porous bag 14 to embrace the human foot toe in cooperation with the bag 14. Each of the three porous bags 13, 14 and 15 is formed of a coarsely woven fabric or a sheet of any suitable porous material and has a number of small holes 16 therein distributed throughout the whole area of the bag. The porous bags 13, 14 and 15 are each sewn to the above-described portions of the base sheet 11 and toe cover 12, respectively except for one edge or the straight edge to provide an opening of the associated porous bag for the purpose to be described hereinafter.

Reference numeral 20 denotes exothermic agent adapted to be received in the porous bags 13, 14 and 15 to perform exothermic reaction with the open air upon contacting the air. For convenience in the handling of the exothermic agent 20, the agent is usually in the form of powder or particle. The powdery or particle exothermic agent comprises a mixture of metal powder such as iron powder and an oxidizing catalyst such as active carbon, saline matter or moisture and when the agent contacts the open air, the metal powder performs exothermic reaction with the open air to be oxidized thereby through the intermediation of the oxidizing catalyst. Prior to the use of the exothermic agent, the agent is piecemeal contained in a porous paper bag 20 having a capacity, for example and the paper bag is then placed in an airtight bag such as an aluminum foil bag 22 for storage. In use, the paper bag 21 is taken out of the storage aluminum foil bag 22 and the exothermic agent 20 in the porous bag 21 is inserted into each of the porous bags 13, 14 and 15 through the opening of the bag 13, 14 or 15.

With the above-mentioned construction and arrangement of the components of the heat insulating insert of the invention, in use, the insulating insert 10 can be easily placed in a conventional footwear requiring no tool and processing work on the part of the footwear.

And in the heat insulating insert 10 of the invention, since the exothermic agent 20 is present on the top and bottom of the toe of the user's foot and also on the plantar arch of the user's foot when the user gets into the footwear having the heat insulating insert 10 placed in position therein, the particular human foot parts or the toe and plantar arch where the human foot feels most chilly among the various parts of the human body are kept warm through the exothermic reaction between the exothermic agent and open air. Especially, the exothermic agent present in the portion of the base sheet 11 corresponding to the plantar arch of the human foot presses against the plantar arch while the footwear user is walking and thus, provides the dual effect of heating and massage to accelerate blood circulation in the foot which is in contact with the heat insulating insert to thereby keep the whole foot warm.

Furthermore, in order to keep the foot warm, the heat insulating insert employs the exothermic agent which performs exothermic reaction with the open air upon contacting the air, the heating provided by such exothermic reaction is not that by burning flame, but moderate and safe. As it will be appreciated, when the exothermic agent 20 has lost its activity after the use of the heat insulating insert 20 for a prolonged time period, the exothermic agent in the paper bag 20 is taken out of the porous bag 13, 14 or 15 and replaced by a new paper bag 20 containing the active exothermic agent 20.

While only one embodiment of the invention has been shown and described in detail, it will be understood that the same is for illustration purpose only and not to be taken as a definition of the invention, reference being had for this purpose to the appended claims.

What is claimed is:

1. A heat insulating insert for a footwear comprising a main body which includes a base sheet having a shape substantially conforming with the shape of the sole of a human foot and a toe cover at the toe-shaped end of said base sheet corresponding to the toe of said human foot; and permeable bags positioned in said toe portion and a portion of said base sheet corresponding to the plantar arch of said human foot and on the inner surface of said toe cover and each containing exothermic agent which performs exothermic reaction with the open air upon contacting the open air, said permeable bags at said toe shaped-end of the base sheet and on the inner surface of said toe cover being in opposing and spaced relationship to each other to embrace said toe of the human foot.

2. The heat insulating insert for a footwear as set forth in claim 1, in which said base sheet and cover sheet are each formed of a sheet of leather, felt or synthetic rubber or a laminated structure of one or more of said leather, felt and synthetic rubber.

3. The heat insulating insert for a footwear as set forth in claim 1, in which said base sheet is formed of a non-woven fabrics.

4. The heat insulating insert for a footwear as set forth in claim 1, in which when said base sheet and toe cover are each formed of leather material, said leather material is provided with a number of small holes to provide a permeability to the base sheet and toe cover.

5. The heat insulating insert for a footwear as set forth in claim 1, in which said exothermic agent comprises a mixture of powdery or particle metal powder and oxidizing catalyst and performs exothermic reaction with the open air upon contacting the air.

6. The heat insulating insert for a footwear as set forth in claim 5, in which said powdery or particle metal is iron powder.

7. The heat insulating insert for a footwear as set forth in claim 1, in which said permeable bags for exothermic agent each has a semi-circular shape and sewn to said base sheet and toe cover except for the straight edge of the bag to provide an opening through which said exothermic agent is inserted into the associated permeable bag.

8. The heat insulating insert for a footwear as set forth in claim 1, in which said permeable bags are each formed of a coarsely woven fabric or a sheet provided with a number of small holes.

* * * * *